United States Patent [19]

Beineke

[11] Plant 4,542

[45] Jun. 10, 1980

[54] DISTINCT VARIETY OF BLACK WALNUT TREE

[75] Inventor: Walter F. Beineke, West Lafayette, Ind.

[73] Assignee: Purdue Research Foundation, West Lafayette, Ind.

[21] Appl. No.: 939,834

[22] Filed: Sep. 5, 1978

[51] Int. Cl.[2] ..... A01H 5/00

[52] U.S. Cl. ..... Plt./32

[58] Field of Search ..... Plt./32

*Primary Examiner*—Robert E. Bagwill
*Assistant Examiner*—James R. Feyrer
*Attorney, Agent, or Firm*—John R. Nesbitt

[57] ABSTRACT

A new and distinct cultivar of black walnut tree (*Juglans nigra L.*) which is distinctly characterized by rapid growth rate, strong central stem tendency, and outstanding straightness for timber purposes. The nut-bearing habits of this tree are unknown. It has not borne either pistillate or staminate flowers during the first 7 years after grafting. The strong central stem tendency is due to the ability of the terminal bud to flush and outgrow the laterals. This variety also has good anthracnose resistance. This particular variety was discovered by the applicant near Martinsville, Ind. in a cultivated area. It occurred as a wild tree growing on land managed for timber-growing purposes and was discovered in the course of a search for unique and high quality black walnut trees to be utilized in breeding for outstanding timber qualities. This selection has been designated as BW132 in records maintained on the performance of grafts made from the original selection at Purdue University and will be known henceforth as "Purdue 3".

4 Drawing Figures

BACKGROUND OF THE INVENTION

Figure 1:
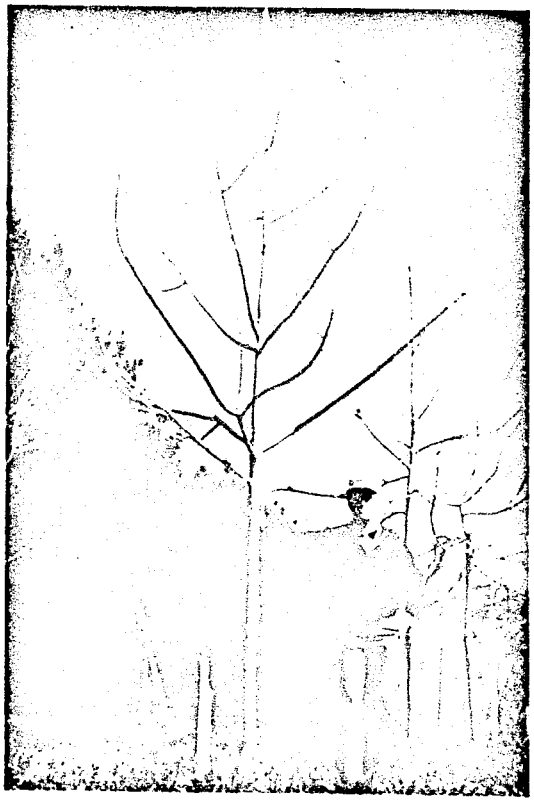
FIGS. 1 through 4 are photographic reproductions in color of the tree showing its timber form.
Figure 2:
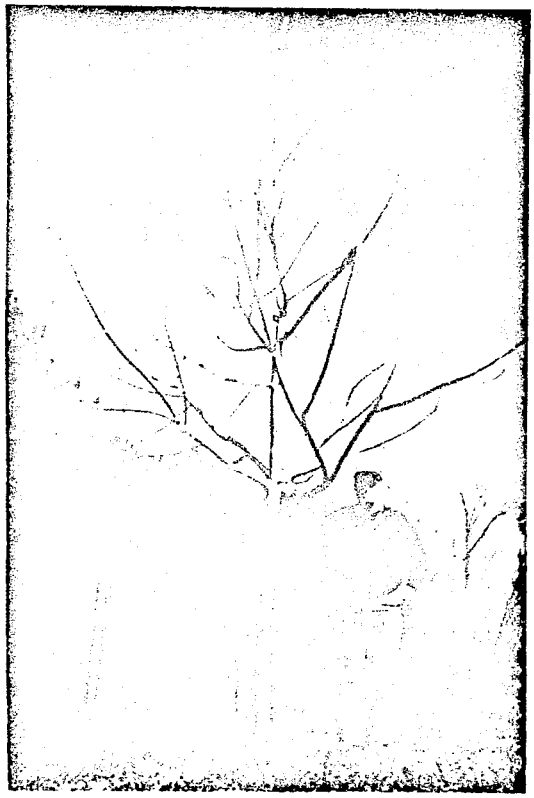
Figure 3:
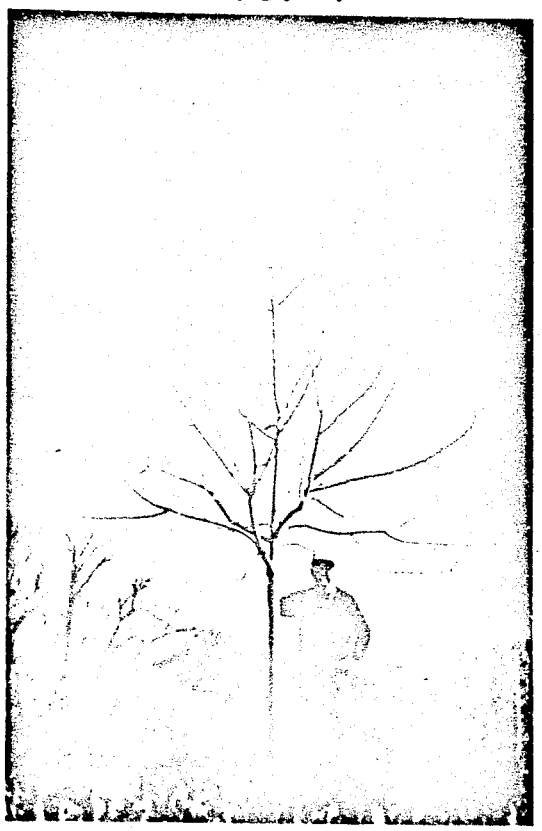
Figure 4:
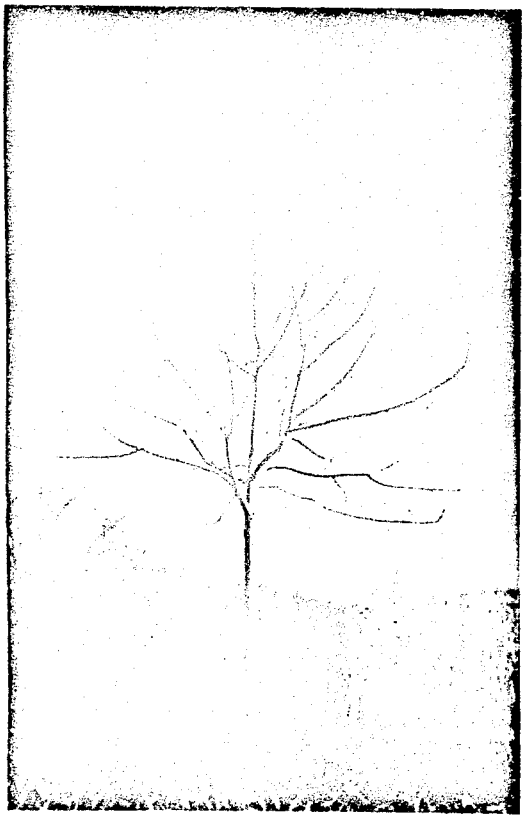

After the selection of the original clone, scions were collected from it and grafted onto common black walnut root-stocks at Martell Forest, Purdue University. These asexual reproductions ran true to the parent tree and to each other in all respects.

DETAILED DESCRIPTION OF THE INVENTION

The botanical details of this new and distinct variety of walnut tree are as follows:

Tree:

*Size.*—Large.

*Vigor.*—Vigorous.

*Growth rate.*—Rapid growth — 29% larger in diameter than average, 3% taller than average, and 45% more cubic foot volume than average at 6 years of 41 clones.

*Form.*—Excellent timber form — 35% straighter than average. Due to the lateness of leafing-out, the terminal bud is seldom if ever killed by late spring frosts, thus, the terminal bud flushes and outgrows the laterals preventing forks from forming. A compact pyramid-shaped crown develops.

Trunk:

*Bark.*—Dark brown to gray.

*Texture.*—Interlacing ridges.

Branches:

*Diameter.*—Average.

*Length.*—Longer than average.

*Branch angle.*—Lower branches — 56° about average.

Foliage:

*Quantity.*—Abundant.

*Density.*—Heavy.

Leaves:

*Compound leaves.*—Size — average; average length 17".

*Leaflets.*—Size — large; average length — $4\frac{3}{8}$"; average width — $1\frac{3}{8}$". Shape — lanceolate; acutely pointed. Thickness — thin; texture — smooth; margin — serrated; petiole — short; color — topside — darkgreen; underside — light green.

*Anthracnose resistance.*—Good resistance — 14% better than average.

*Time of leafing.*—Extremely late — averages 14 days later or 126% later than average.

Flowering habit: No pistillate or staminate flowers have been produced during the first 7 years after grafting.

What is claimed is:

1. A new and distinct variety of black walnut tree substantially as illustrated and described, which has excellent timber quality, is fast growing, has strong central stem tendency due to the ability of the terminal bud to flush and outgrow the laterals, little sweep, extremely late in time of leafing.

* * * * *